US00PP09368P

United States Patent [19]

Nies

[11] Patent Number: Plant 9,368

[45] Date of Patent: Nov. 14, 1995

[54] CHERRY TREE 'EARLY RED'

[76] Inventor: Marvin L. Nies, 9296 E. Kettleman, Lodi, Calif. 95240

[21] Appl. No.: 383,925

[22] Filed: Feb. 6, 1995

[51] Int. Cl.[6] ..... A01H 5/00

[52] U.S. Cl. ..... Plt./37

[58] Field of Search ..... Plt./37

[56] References Cited

U.S. PATENT DOCUMENTS

| | | | |
|---|---|---|---|
| P.P. 4,431 | 6/1979 | Nies | Plt./37 |
| P.P. 4,436 | 7/1979 | Nies | Plt./37 |
| P.P. 8,721 | 5/1994 | Calder | Plt./37 |

*Primary Examiner*—James R. Feyrer

[57] ABSTRACT

The present invention relates to a cherry tree and more particularly to a new and distinct variety broadly characterized by a tree of medium size and vigor, upright, vase formed, hardy, foliated with large, ovate, abruptly acuminate, acutely pointed, moderately coarse crenate leaves, that is inclined to be a very regular, very precocious bearing tree, with a lower chilling requirement than any commercial variety known to me presently grown in the United States, blooming approximately five (5) days ahead of Ruby (U.S. Plant Pat. No. 4,436), a low chilling variety, in my experimental orchard located near Lodi, County of San Joaquin, Calif., and four (4) days ahead of Tulare (patented), in my test plot in Orange Cove, County of Fresno, Calif. The present variety has very short stems, very firm textured fruit, being equal in firmness to mid-season commercial varieties, resembling Garnet (U.S. Plant Pat. No. 4,431) in fruit shape, maturing in Lodi, Calif., the first week of May, with full uniform maturity on May, 2, 1993, the fruit being uniformly large, having excellent flavor, excellent soluble solids, moderate acidity, very agreeable sugar-acid ratio, very glassy external appearance being shiny red over the total area of the fruit, semi-free in type and with fruit flesh that is very dark, inky, red in color when the fruit attains dark red maturity. The variety was developed as a hybridized seedling of Garnet as the selected seed parent and Ruby as the selected pollen parent.

1 Drawing Sheet

FIELD OF INVENTION

The present variety of cherry tree has been denominated varietally as "Early Red", however, it is anticipated that this variety of cherry tree, along with the fruit produced, will be marketed under the Trademark "Early Garnet". This variety is the outgrowth of a plant breeding program which has been conducted by me on a continuous basis since 1957 in my Experimental orchard near Lodi, County of San Joaquin, Calif.; the purpose of which program has been to develop new and distinct varieties of cherry trees for commercial growing of fruit in warmer, lower chilling, earlier production areas, the tree to have good heat tolerance, fruit that is large, firm, early ripening, with a classy appearance, resistant to the development of suture, spurs, doubles, outstanding flavor, non-astringent, non-browning skin and flesh, adequate disease and insect resistance, with higher than normal soluble solids and medium acidity. The present variety has achieved these objectives. This variety of cherry tree is embraced by Subclass 37, Plants, of the Plant Patent Office Manual Of Classification.

PRIOR VARIETIES

Among the existing varieties of cherry trees which are known to me are those mentioned herein; to-wit Mahaleb rootstock (unpatented), Colt rootstock (U.S. Plant Pat. No. 4,059), Tulare (U.S. Plant Pat. No. 6,407), Garnet (U.S. Plant Pat. No. 4,431), Ruby (U.S. Plant Pat. No. 4,436). Hative de Burlat (Unpatented), Bing (unpatented), and Brooks (U.S. Plant Pat. No. 6,676).

ORIGIN OF THE VARIETY

The present variety, denominated varietally as "Early Red", relates to a distinct variety of cherry tree originated by me, the fruit of which was first observed by me in 1982 in the seedling block in my experimental orchard in Lodi, County of San Joaquin, Calif. The present variety developed by me in a cultivated area of my experimental orchard at the Marvin L. Nies Ranch near Lodi, County of San Joaquin, Calif., was initiated in 1976 by crossing the selected seed parent Garnet with the selected pollen parent Ruby, which resulted in seeds from the seed parent, which when germinated and grown, produced a large number of seedlings, one of which was the present variety; the location of which in the seedling block was recorded in my Breeding Records as Seedling T 7-64-2, and which when grown to maturity, evidenced novel and distinctive characteristics, and I therefore selected it for asexual reproductions preparatory to patenting and ultimate commerical growing thereof.

ASEXUAL REPRODUCTION OF THE VARIETY

Subsequent to the origination of the present variety of cherry tree, I asexually reproduced the selection on Mahaleb (unpatented) and Colt (U.S. Plant Pat. No. 4,059) rootstocks in my experimental orchard near Lodi, County of San Joaquin, Calif., by budding and grafting, and such reproduction of plant and fruit characteristics were true to the original plant at maturity in all respects.

SUMMARY OF VARIETY

My first observation of the fruit of this variety was made in 1982 in my experimental orchard seedling block in Lodi, San Joaquin County, Calif. What set the present variety apart from the other seedlings was that it bloomed very early indicating a low chilling cultivar, had very firm fruit that was firmer than Ruby, equal in firmness to the very firm early mid-season Garnet and mid-season Bing, considereably firmer than the medium firm Brooks; with a very short thick stem, exceedingly dark red flesh and juice, resistance to suture, spurring, and doubling of the fruit, excellent flavor, fruit form similar to the seed parent Garnet, a very desirable shiny, glassy appearing fruit, and with a lower chilling requirement than that of any cherry variety known to me grown commercially in California. All of the above enumerated desirable qualities converging in one seedling made this selection a candidate for the ultimate commercial growing thereof. This variety's unusually firm fruit combined with earliness in ripening, is in my experience as a breeder of new cherry varieties, genetically out of the norm. All early ripening cherry varieties, known to me, are soft; indicating a genetic link between softness and early ripening. The quite firm Ruby cherry, which ripens seven (7) days after the very soft, early maturing Hative de Burlat cherry variety; is the earliest firm commercial cherry variety presently grown in California. The present variety is six (6) days earlier in maturity than Ruby, on (1) to two (2) days later than Hative de Burlat and four (4) days earlier than Brooks (patented). The heat tolerance of the tree, firmness of the fruit, very short stems, (which should minimize damage to the fruit during periods of high winds), resistance to suture, spurs, and doubling; creates an opportunity to grow higher quality, firm early cherries, not only in the present higher chilling commercial production areas, but also in the lower chilling, windier, low humidity, higher temperature locations. The present variety is very precocious, being similar to Ruby the pollen parent, coming into bearing one year earlier than most standard varieties. Garnet, the seed parent, by comparison is slower to bear fruit, especially on young vigorous trees. It is anticipated that limiting the number of pollenizers, more severe pruning of the trees, especially in warmer, drier climates, will be necessary to obtain larger sized fruit that is more desirable in the marketplace.

DRAWING

The accompanying photograph exhibits six (6) whole fruits positioned to display the characteristics of the skin color and form, on a representative branch with leaves.

POMOLOGICAL CHARACTERISTICS

The botanical details of this new and distinct variety of cherry tree—with color definitions (except those in common color terms) referenced to The Wilson Colour Chart I and II, published by the British Colour Council—Horticultural Color Chart (1938) are as follows:

Tree:
- *Size.*—Medium.
- *Vigor.*—Medium.
- *Growth.*—Upright-spreading.
- *Density.*—Dense.
- *Form.*—Vase-formed.
- *Hardiness.*—Hardy.
- *Production.*—Very precocious.
- *Bearing.*—Very regular bearer.

Trunk:
- *Size.*—Stocky.
- *Texture.*—Medium.

Branches:
- *Size.*—Stocky.
- *Texture.*—Medium.
- *Color.*—Reddish brown on younger growth. Gray dull on older wood.
- *Lenticals.*—Number: numerous. Size: Medium large. Orientation — perpendicular to the edge of the branch.

Leaves:
- *Size.*—Large. Average length (25 leaves) 15.2 cm. Average width (25 leaves) 7.5 cm.
- *Form.*—Ovate. Abruptly acuminate. Acutely pointed.
- *Thickness.*—Thick.
- *Color.*—Top of leaf-dark green. Bottom of leaf-light green.
- *Texture.*—Smooth.
- *Margin.*—Crenate.
- *Petiole.*—Medium length — averaging 4.2 cm in length. Medium thickness. Pigmented — Dahlia Purple (P 9/31).
- *Glands.*—Number-variable-usually four (4) — sometimes six (6). Compressed. Mostly mixture of alternate-opposite configurations — occasionally on some petioles, glands are opposite some alternate. Large. Light red. Positioned on petiole adjacent to blade.
- *Stipules.*—Two (2) — one (1) on each side of petiole.

Flower buds:
- *Hardiness.*—Hardy.
- *Size.*—Medium.
- *Length.*—Medium.
- *Form.*—Conic.

Flowers:
- *Date of bloom.*—Mar. 10, 1993. Very early compared to standard varieties.
- *Petals.*—Size: Medium. Length — 17 mm. Width — 16 mm. Color — Pure white, Iridescent. Conspicuously veined, with shell like appearance. Petals significantly separated from each other on the hypanthium barely touching further removed in the corolla. Mostly notched at the apex and with small, widely spaced serrations ⅓ distance back from apex.
- *Filament length.*—1 cm.
- *Stigma length.*—1.5 cm.
- *Hypanthium.*—Medium-five (5) sepals-strongly reflexed on older flowers.
- *Blooming period.*—Compact-no straggle bloom-resulting in even maturity.

Fruit:
- *Maturity when described.*—Eating ripe — May 2, 1994.
- *Date of first picking.*—May 2, 1994. All fruit picked at one time.
- *Size.*—Very uniform. Large. Average diameter — 2.6 cm. Average size in suture plane — 2.2 cm.
- *Form.*—Uniform, Symmetrical transversely in the suture plane. Globose — broadly oblate. Depressed at the apex-with the depression extending a short distance up the suture line. Compressed in the suture plane.
- *Suture.*—Shallow. Inconspicuous. Extends from base beyond apex.
- *Ventral surface.*—Rounded strongly from base to near apex. Narrow dark red pigmented line from base to apex.
- *Stem cavity.*—Flaring and circular. Rounded. Elongated in suture plane.
- *Color.*—Dark red when fully mature.
- *Base.*—Rounded. Truncate.
- *Apex.*—Short. Rounded.
- *Pistil point.*—Apical. An Inconspicuous brown abscission point.
- *Ripening span.*—Very even ripening. One picking.

Skin:
- *Thickness.*—Medium.
- *Texture.*—Medium.
- *Tenacity.*—Tenacious to flesh.
- *Tendency to crack.*—None in dry weather. Some to significant amounts in certain years during wet weather conditions.

*Color.*—Currant Red (8/21) — mature fruit. Narrow — very dark red stripe (Garnet Lake 8/28) on ventral surface from base to apex.

*Down.*—Wanting.

*Surface.*—Glassy-shiny.

Flesh:

*Color.*—Very dark red (Currant Red 821/2) — fully mature fruit.

*Surface of pit cavity.*—Very dark red. Currant Red (821).

*Amygdalin.*—Wanting.

*Texture.*—Firm-fine-crisp.

*Aroma.*—Wanting.

*Fibres.*—Few-Fine.

*Ripens.*—Evenly.

*Flavor.*—Excellent at full maturity.

*Eating quality.*—The best. Excellent soluble solids. Moderate acidity.

*Tendency to crack.*—None in dry weather. Some to significant amounts under certain wet weather conditions.

Stone:

*Type.*—Semi-free.

*Size.*—Medium. Average length — 1 cm. Average width — 1 cm. Average breadth — 8.5 mm.

*Form.*—Globose-oval.

*Base.*—Straight-oblique.

*Hilum.*—Narrow. Oblong.

*Apex.*—Rounded.

*Sides.*—Equal.

*Surface.*—Smooth from dorsal edge to ridged ventral surface — broadly furrowed on smooth surface ¼ of the distance from base to apex.

*Ridges.*—Jagged.

*Ventral Edge.*—Thick-with wing towards base.

*Dorsal Edge.*—Narrow ridge.

*Color.*—Egyptian Buff (407/1).

*Form.*—Oval.

*Taste.*—Very bitter.

*Viability.*—Very low.

*Amygdalin.*—Abundant.

Use: Market — dessert — shipping.

Keeping quality: Good.

Resistance to insects and diseases: No unusual susceptibilities noted.

Shipping quality: Good — both local and long distance.

Variance in botanical details: Although the new variety of cherry possesses the described characteristics under the ecological conditions at Lodi, Calif., in the Northern part of the San Joaquin Valley, it is to be expected some variations in these pomological characteristics may occur when grown in areas with different climatic conditions, different soil types, and/or varying cultural practices.

I claim:

1. A new and distinct variety of cherry tree, substantially as illustrated and described, being of medium vigor and size, the fruit strongly resembling Garnet in form, size, color and external appearance, but having a somewhat shorter thicker fruit stem, equivalent firmness of flesh and toughness of the skin, darker red flesh color and darker red juice at maturity, fruit ripening more evenly, picking ripe twelve (12) days earlier, having a lower chilling requirement, more precocious, the tree having equivalent tolerance for higher temperatures with good resistance to the development of spurs and doubles, but being more resistant to the development of sutures in warmer climates.

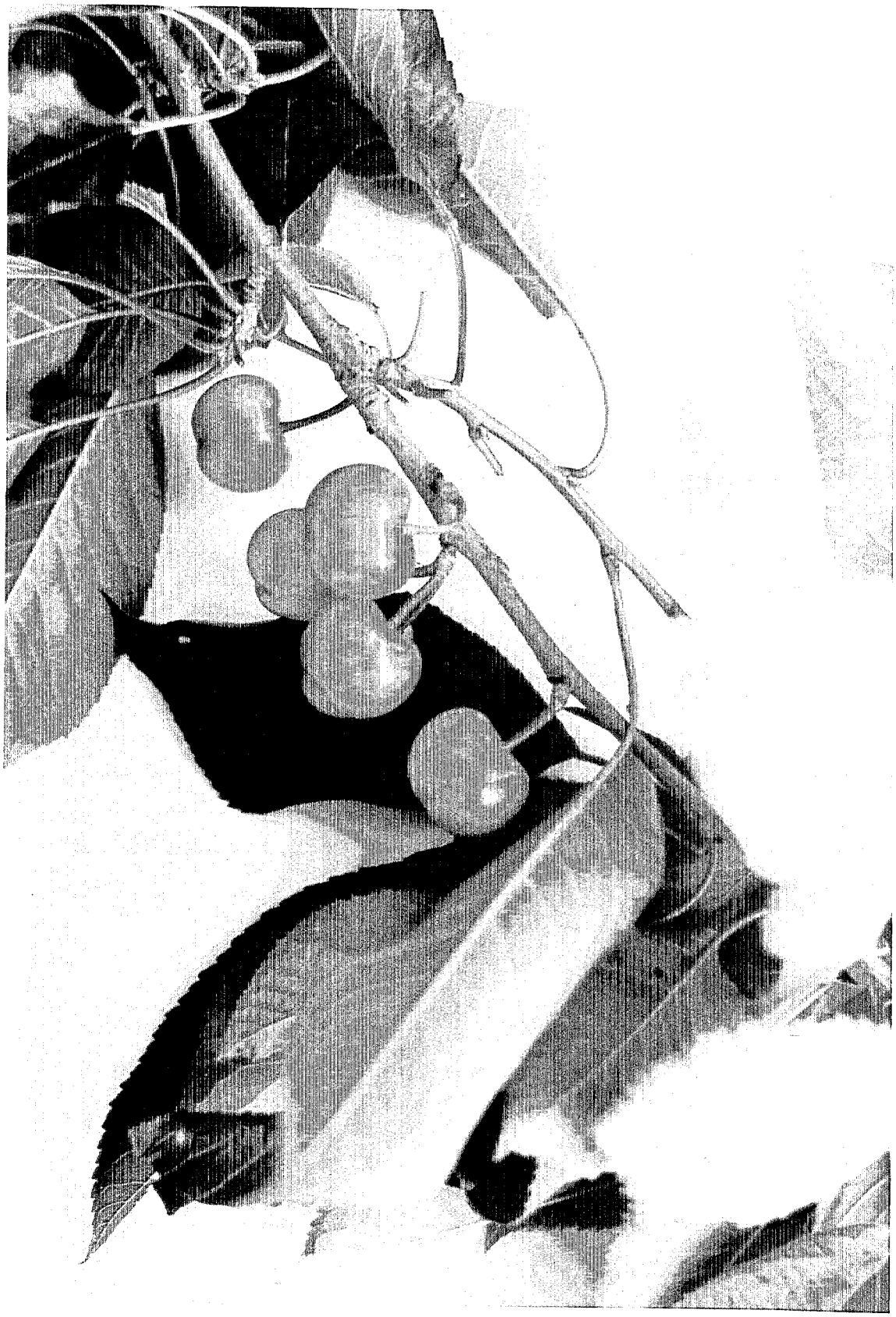

* * * * *